(12) United States Patent
Tamai et al.

(10) Patent No.: US 7,807,107 B2
(45) Date of Patent: Oct. 5, 2010

(54) PARTICLE AGGLUTINATION-EVALUATING CONTAINER

(75) Inventors: Toyohiro Tamai, Hachioji (JP); Hitoshi Narita, Matsudo (JP); Yasunobu Kaneko, Hachioji (JP); Yumi Kobayashi, Tokyo (JP)

(73) Assignee: Beckman Coulter, Inc., Brea, CA (US)

( * ) Notice: Subject to any disclaimer, the term of this patent is extended or adjusted under 35 U.S.C. 154(b) by 216 days.

(21) Appl. No.: 12/026,142

(22) Filed: Feb. 5, 2008

(65) Prior Publication Data

US 2008/0213131 A1 Sep. 4, 2008

Related U.S. Application Data

(63) Continuation of application No. PCT/JP2007/061263, filed on Jun. 4, 2007.

(30) Foreign Application Priority Data

Jun. 5, 2006 (JP) ............................. 2006-156266

(51) Int. Cl.
*G01N 33/00* (2006.01)
*G01N 33/48* (2006.01)

(52) U.S. Cl. ............................ 422/73; 422/58; 422/102; 435/13; 435/288.3

(58) Field of Classification Search ................... 422/73; 435/288.3, 13
See application file for complete search history.

(56) References Cited

U.S. PATENT DOCUMENTS 4,290,997 A * 9/1981 Suovaniemi ................. 422/73
4,303,616 A 12/1981 Kano et al.
4,466,740 A * 8/1984 Kano et al. .................. 356/246
5,017,341 A * 5/1991 Takekawa .................... 422/102
5,338,689 A 8/1994 Yves et al.

FOREIGN PATENT DOCUMENTS

| DE | 100 61 515 A1 | 6/2001 |
| EP | 0 725 276 A1 | 8/1996 |
| JP | 54-130195 | 10/1979 |
| JP | 58-754 | 1/1983 |
| JP | 61-44268 | 10/1986 |
| JP | 63-60854 | 11/1988 |

(Continued)

*Primary Examiner*—Jill Warden
*Assistant Examiner*—Jennifer Wecker
(74) *Attorney, Agent, or Firm*—Townsend and Townsend and Crew LLP (57) ABSTRACT

A particle agglutination-evaluating container for immunological analysis, based on an agglutinate formed in an agglutination reaction between an antibody- or antigen-containing sample and agglutination particles, includes a transparent container body having a bottom face including a sloping bottom face and a raised bottom face extended in a horizontal direction at the top of the sloping bottom face to form an obtuse angle with the sloping bottom face, and a fluidal separation layer containing insoluble particles which are filled in the container body and where the agglutination particles are separated according to the agglutination degree, wherein agglutination is evaluated by observation from the bottom of the container body, where the agglutination reaction is judged positive when the agglutination particles are observed through the raised bottom face, negative when observed at the bottom end of the sloping bottom face, and weakly positive when observed in the middle of the sloping bottom face.

15 Claims, 7 Drawing Sheets

FOREIGN PATENT DOCUMENTS

| | | |
|---|---|---|
| JP | 4-285858 | 10/1992 |
| JP | 7-294528 | 11/1995 |
| JP | 8-7215 | 1/1996 |
| JP | 2001-201505 | 7/2001 |
| JP | 2004-20535 | 1/2004 |

* cited by examiner

PRIOR ART

FIG. 12

PRIOR ART

FIG. 13

PARTICLE AGGLUTINATION-EVALUATING CONTAINER

CROSS REFERENCE TO RELATED APPLICATIONS

This is a Continuation Application of PCT Application No. PCT/JP2007/061263, filed Jun. 4, 2007, which was published under PCT Article 21(2) in Japanese.

This application is based upon and claims the benefit of priority from prior Japanese Patent Application No. 2006-156266, filed Jun. 5, 2006, the entire contents of which are incorporated herein by reference.

BACKGROUND OF THE INVENTION

1. Field of the Invention

The present invention relates to a particle agglutination-evaluating container for use in evaluation of a particle agglutination pattern in an immunological agglutination reaction. In particular, the present invention relates to a particle agglutination-evaluating container for evaluation of various blood types or detection of an antigen or antibody, based on the agglutination pattern of blood cell particles.

2. Description of the Related Art

Conventionally, immunological agglutination reactions such as antigen-antibody reactions have been examined using a test tube as the reaction container. In such an examination, antigen-bound latex particles or antigen-presenting red blood cell particles and an antigen-reactive antibody are mixed in a test tube to form a particle-antibody agglutinate; the agglutinate is allowed to precipitate spontaneously or by centrifugation; and then the precipitate is loosened by shaking the test tube to evaluate the agglutination reaction. If the precipitate is not loosened, the reaction is evaluated as positive, and if loosened, it is evaluated as negative. However, in the examination method, it is difficult to identify an intermediate reaction (weakly positive reaction) between the positive and negative reactions with the naked eye. In addition, when a large number of samples are examined, the examination method requires an increased number of test tubes and thus the operation is troublesome.

In the examination of a great number of samples, a reaction container having multiple V- or U-bottomed wells such as a microplate has been generally used. Also in the examination using such a reaction container, the particle-antibody agglutinate is allowed to precipitate as described above. If the particle-antibody agglutinate is not loosened, then the agglutinate is captured on the bottom face of the reaction container, thereby forming a pattern of the particles spread on the bottom face (positive). On the other hand, if the agglutinate is loosened, then the particle gathers on the lowest region of the bottom face of the reaction container (negative). An intermediate reaction (weakly positive reaction) is detected as an intermediate agglutination pattern. The method enables visual or optical observation of the agglutinate captured on the bottom face of the reaction container microplate from above or below the microplate, and thus it is suitable for the examination of a great number of samples. However, the capturing efficiency of the agglutinate on the microplate bottom face depends significantly on the condition of the bottom face. Although the agglutinate should stably adhere to the bottom face in the examination, a weak agglutinate easily slides from an unprocessed smooth bottom face, indicating a false negative.

As described in Jpn. Pat. Appln. KOKOKU Publication Nos. 61-44268 and 63-60854, studies has been conducted aimed at improving the agglutinate-capturing efficiency by forming unevenness on the bottom face of the reaction container or by roughening the surface of the bottom face. Although there was some improvement in the agglutinate-capturing efficiency by the method, there is a limit on the agglutinate-capturing efficiency only with the bottom face of a well. In addition, blood cells are precipitated spontaneously in the method, and thus the method requires an extended period of time for the examination.

Recently, a container filled with insoluble particles was developed for more efficient capturing of the agglutinate. The passive agglutination method using the container is generally called a microcolumn agglutination method.

Figure 12:
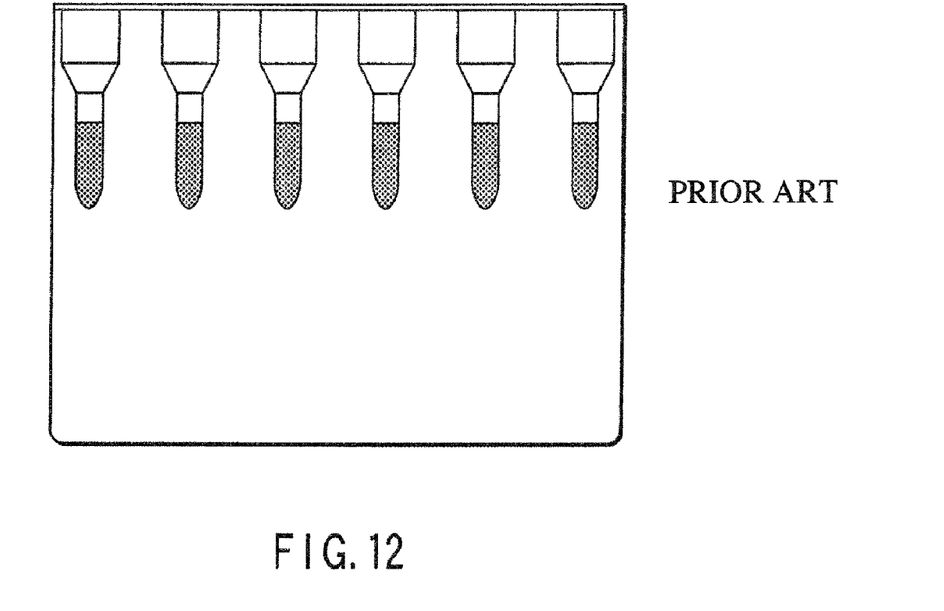
FIG. 12 is a side view illustrating a prior-art particle agglutination-evaluating container.

As described in Jpn. Pat. Appln. KOKOKU Publication No. 8-7215, Y. Lapierre et al. developed a reaction container, which consists of a card and rod-shaped microreaction tubes formed thereon, wherein the tubes are filled with insoluble particles, such as polymer or glass particles, having a diameter of 10 to 200 μm, and which allows efficient differentiation between agglutinated and unagglutinated red blood cells by centrifugation. A side view of the reaction container is shown in FIG. 12. In addition, EP725276 discloses a similar reaction container filled with glass beads. These devices have a characteristic in that immunologically inactive insoluble particles are used. In both the devices, multiple rod-shaped microreaction tubes filled with insoluble particles are embedded in a plate-shaped plastic plate, and each microreaction tube is used as it is held upright in the vertical direction. During assay, a liquid sample is injected through an inlet on top of the microreaction tube standing in the vertical direction; the container is centrifuged after reaction; and the agglutinate captured by the insoluble particles is detected visually or optically from the side wall. Presence of the agglutinate on the insoluble particles indicates positive reaction; presence of the agglutinate in the intermediate layer of the insoluble particles indicates weak positive reaction; and precipitation of the agglutinate to below the insoluble particles indicates negative reaction.

The rod-shaped microreaction tube described above has advantages that it is possible to complete the reaction in a shorter period of time by using centrifugation, and the evaluation is also easy, because the agglutination pattern differs significantly between the positive and negative reactions. However, because the agglutination pattern develops in the vertical direction and the insoluble particle layer is opaque, it is not possible to examine the reaction in the direction from above or below and thus, the observation is only made through the side wall. Therefore, in observation of the agglutinates on multiple cards, it was necessary to hold up and evaluate each card separately by visually viewing it horizontally, causing a significant obstacle to high-throughput analysis in an automatic analyzer.

To solve the problem above and examine a great number of samples by the microcolumn agglutination method, German Patent No. 10061515 discloses a microplate-shaped container having multiple reaction chambers, of which at least part of the bottom face is narrowed and which is filled with insoluble particles. The container enables acquisition of a flat-spread pattern of the agglutinate when the reaction is positive, and a pattern in which the non-agglutinate gathers in the narrowed region when it is negative, thus allowing observation both from above and below. However, the method still had a problem that it was not possible to detect the pattern accurately in the direction from above or below, especially when the reaction is weakly positive.

Figure 13:
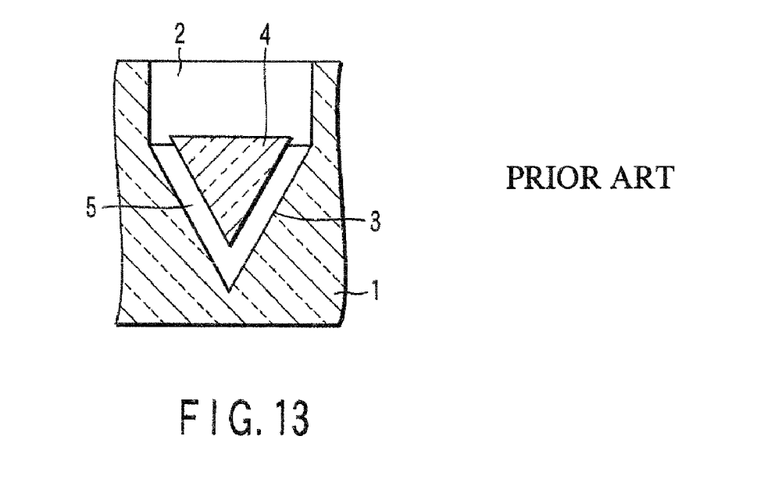
FIG. 13 is a sectional view illustrating another prior-art particle agglutination-evaluating container.

Further, Jpn. Pat. Appln. KOKOAI Publication No. 2004-20535 discloses a container allowing detection of the agglutination pattern from the bottom. The cross section of the container is shown in FIG. 13. FIG. 13 shows that, in a transparent container main body 1 having a V-bottomed well 2, a spacer 4 having a lower face facing the bottom face of the well in parallel is placed so that there is a gap layer on a bottom face 3 of the well. Insoluble particles are filled in the gap layer formed between the spacer and the bottom face of the well, forming a fluidal separation layer 5. Presence of the agglutinate on the fluidal separation layer indicates positive reaction; presence of the agglutinate in the intermediate layer of the fluidal separation layer indicates weak positive reaction; and presence of the agglutinate at the bottom of the well indicates negative reaction. It is possible to observe and identify each agglutination pattern in the direction from below the well bottom face 3.

However, it is not easy to form such a V- or U-shaped space while placing a spacer as it floats inside the reaction container, because it requires an additional support material for supporting the spacer. It is also difficult to introduce a sample in the V- or U-shaped space of the reaction container evenly, because the sample inlet is circular in shape. If the sample is introduced therein unevenly, it has an adverse effect on the agglutination pattern. In addition, it is difficult to observe the positive-reaction agglutinate in the container shown in FIG. 13, because the bottom of the transparent container main body 1 has a certain thickness.

BRIEF SUMMARY OF THE INVENTION

Under the above circumstances, an object of the present invention is to provide a particle agglutination-evaluating container that allows easy and accurate evaluation of the agglutination pattern and observation thereof in the direction from below the container, thereby enabling high-throughput analysis in an automatic analyzer.

According to one aspect of the present invention, there is provided the following particle agglutination-evaluating container:

(1) A particle agglutination-evaluating container for use in immunological analysis, based on an agglutinate formed in an agglutination reaction between an antibody- or antigen-containing sample and agglutination particles, comprising:

a transparent container main body having a bottom face including a sloping bottom face and a raised bottom face extended in a horizontal direction at the top of the sloping bottom face to form an obtuse angle with the sloping bottom face, and a fluidal separation layer containing insoluble particles which are filled in the transparent container main body and where the agglutination particles are separated according to the degree of agglutination, wherein the agglutination particles form an agglutinate and are located on a top face of the fluidal separation layer when the agglutination reaction is positive, the agglutination particles do not form an agglutinate and migrate to the bottom of the sloping bottom face when the agglutination reaction is negative, and the agglutination particles form an agglutinate and are located in an intermediate region of the fluidal separation layer when the agglutination reaction is weakly positive between positive and negative, and thus agglutination is evaluated by observation from the bottom face side of the transparent container main body, where the agglutination reaction is judged positive when the agglutination particles are observed through the raised bottom face, negative when the agglutination particles are observed at the bottom end of the sloping bottom face, and weakly positive when the agglutination particles are observed in the middle of the sloping bottom face.

According to another aspect of the present invention, there is provided the following particle agglutination-evaluating container:

(2) A particle agglutination-evaluating container for use in immunological analysis, based on an agglutinate formed in an agglutination reaction between an antibody- or antigen-containing sample and agglutination particles, comprising:

a transparent container main body having a bottom face including a sloping bottom face raised in a shape of a truncated cone or pyramid, where the vertex region of the bottom face forms a raised bottom face extended in a horizontal direction; and a fluidal separation layer containing insoluble particles which are filled in the transparent container main body and where the agglutination particles are separated according to the degree of agglutination, wherein the agglutination particles form an agglutinate and are located on a top face of the fluidal separation layer when the agglutination reaction is positive, the agglutination particles do not form an agglutinate and migrate to the bottom of the sloping bottom face when the agglutination reaction is negative, and the agglutination particles form an agglutinate and are located in an intermediate region of the fluidal separation layer when the agglutination reaction is weakly positive between positive and negative, and thus agglutination is evaluated by observation from the bottom face side of the transparent container main body, where the agglutination reaction is judged positive when the agglutination particles are observed through the raised bottom face, negative when the agglutination particles are observed at the bottom end of the sloping bottom face, and weakly positive when the agglutination particles are observed in the middle of the sloping bottom face.

The particle agglutination-evaluating container according to an aspect of the present invention comprises the bottom face having a sloping bottom face and a raised bottom face extended in a horizontal direction at the top of the sloping bottom face to form an obtuse angle with the sloping bottom face, and thus enables easy and accurate observation of the agglutination pattern in the direction from below the container. The particle agglutination-evaluating container according to another aspect of the present invention comprises a bottom face including a sloping bottom face raised in a shape of a truncated cone or pyramid, where the vertex region of the bottom face forms a raised bottom face extended in a horizontal direction, and thus enables easy and accurate observation of the agglutination pattern in the direction from below the container. Therefore, the container according to the present invention eliminates the disadvantage of observation from the side-wall direction and allows evaluation of a large number of samples in an automatic analyzer. In addition, the container according to the present invention, which has a bottom face in a particular shape including a sloping face and a raised face, can be formed easily without the difficulty of placing a particular structure at a particular position, as it floats, in the space of a reaction container.

DETAILED DESCRIPTION OF THE INVENTION

Embodiments of the present invention will be described below with reference to the drawings. In the description below, the same reference numerals are allocated to the same parts in all figures.

First Embodiment

Figure 1:
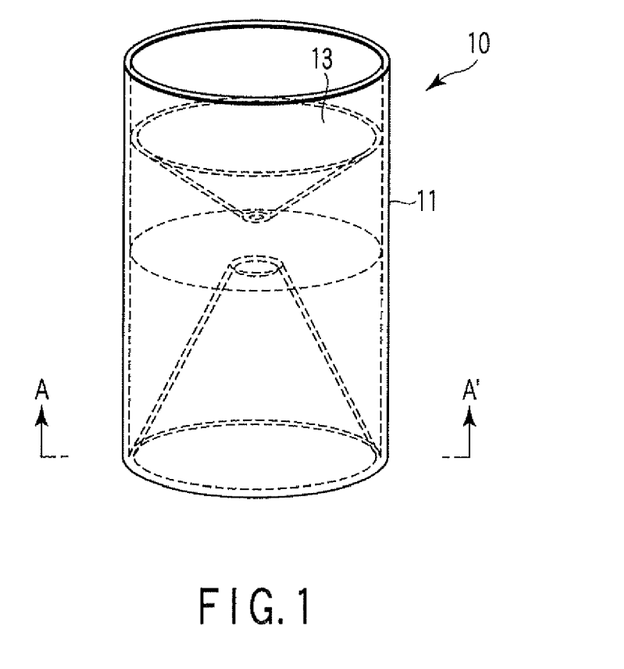
FIG. 1 is a perspective view illustrating a particle agglutination-evaluating container according to a first embodiment of the present invention.
Figure 2:
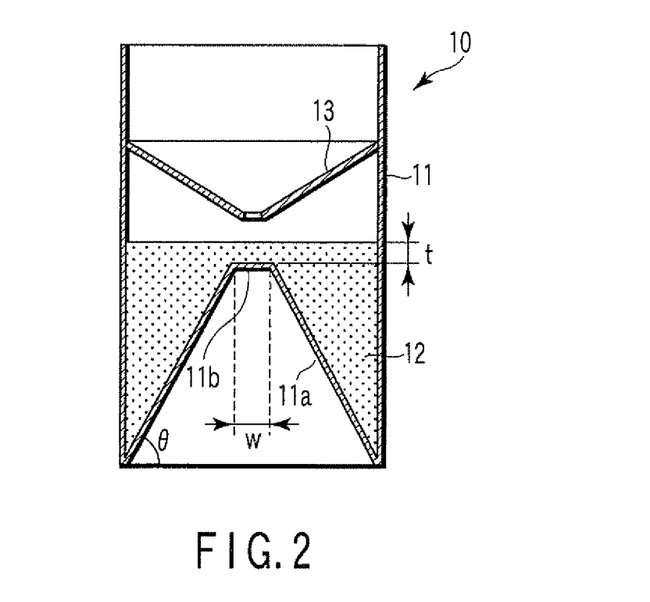
FIG. 2 is a sectional view of the container, when cut along the line A-A' shown in FIG. 1.

FIG. 1 is a perspective view illustrating a particle agglutination-evaluating container 10 according to the first embodiment of the present invention. FIG. 2 is a sectional view illustrating the particle agglutination-evaluating container 10 shown in FIG. 1, when cut along the line A-A'.

A transparent container main body 11 of the particle agglutination-evaluating container 10 is cylindrical in its external shape, and has a bottom face including a sloping bottom face 11a and a raised bottom face 11b extended horizontally at the top of the sloping bottom face 11a to form an obtuse angle with the sloping bottom face. The bottom face has an inverted-V shape of a truncated circular cone, and the raised bottom face 11b is a horizontal face. The transparent container main body 11 is filled with insoluble particles for separating agglutination particles depending on the degree of agglutination, forming therein a fluidal separation layer 12. The transparent container main body 11 has, in its internal wall, a funnel-shaped sample inlet 13 for injecting an antibody- or antigen-containing sample collectively onto the raised bottom face 11b of the transparent container main body 11 (for prevention of addition onto the sloping bottom face 11a).

The transparent container main body 11 is made of a transparent material (for example, transparent resin) so that the agglutination pattern formed between an antibody-containing sample and antigen-immobilized agglutination particles or between an antigen-containing sample and antibody-immobilized agglutination particles can be observed, upward from the bottom side of the transparent container main body 11.

The transparent container main body 11 has a cylindrical external shape in the first embodiment, but may have the shape of a quadrangular prism of which the bottom face is raised into the shape of a truncated quadrangular pyramid. The bottom face of the transparent container main body 11 has an inverted-V shape in the first embodiment, but the raised bottom face in the inverted-V shape may be rounded into an inverted-U shape (see FIGS. 5 and 6).

The gradient angle of the sloping bottom face ($\theta$ in FIG. 2) is preferably 45° to 75°, particularly preferably 55° to 75°, with respect to the horizontal plane. When the sloping bottom face 11a shown in the sectional view of FIG. 2 is curved, the gradient angle can be determined by drawing a tangent line on the curve. If the gradient angle is small, unagglutinated particles accumulate at the bottom and form a broadly spread agglutination pattern, making the judgment of a negative reaction more difficult. On the other hand, if the gradient angle is large, an agglutinate is less likely to be captured on the sloping face, leading to deterioration of agglutinate-capturing efficiency.

Figure 6:
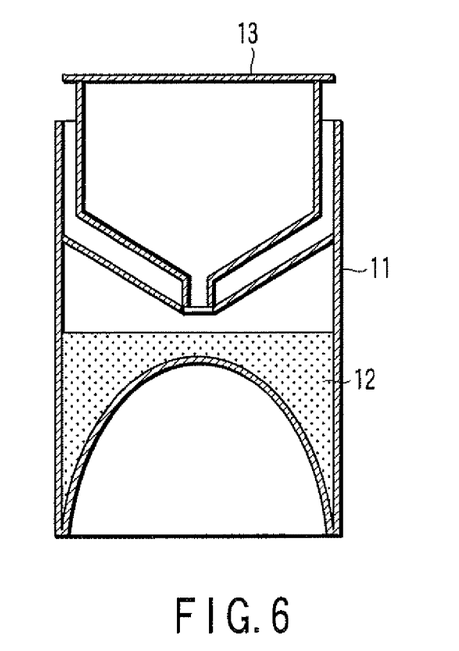
FIG. 6 is a sectional view of a modified example 2 of a particle agglutination-evaluating container according to the first embodiment of the present invention.

The gradient angle of the sloping bottom face may be varied in the same transparent container main body, and may be larger in the region closer to the lower (deeper) end of the sloping bottom face. For example, as shown in FIG. 6, if the gradient angle increases in the region closer to the bottom end of the sloping bottom face and is largest at the bottom face, precipitate of unagglutinated particles (negative agglutination pattern) can be detected more easily.

The sloping bottom face may be surface-roughened for improvement in agglutinate-capturing efficiency. The roughened surface is a surface having roughness suitable for capturing weakly positive agglutinate, and for example, the sloping bottom face may have orderly steps, such as those shown in FIG. 7 (see Jpn. Pat. Appln. KOKOKU Publication No. 61-44268). For example, raised steps different in height by 2 to 50 μm in the vertical direction may be formed orderly on the sloping face at an interval of 5 to 200 μm.

Figure 5:
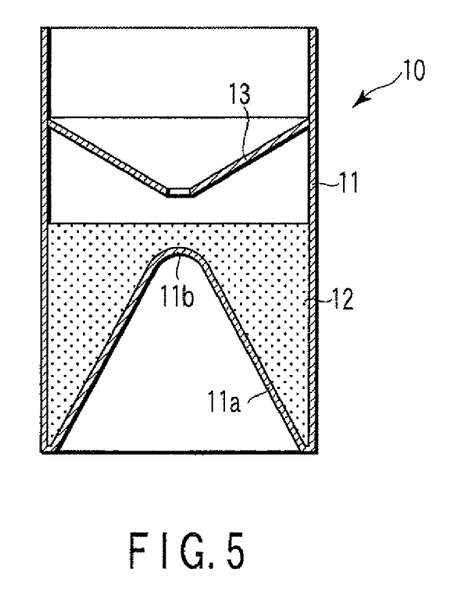
FIG. 5 is a sectional view of a modified example 1 of a particle agglutination-evaluating container according to the first embodiment of the present invention.

The raised bottom face 11b is formed in the horizontal direction at the top of the sloping bottom face 11a, forming an obtuse angle with the sloping face. In the present invention, the raised bottom face 11b may be a flat surface as shown in FIGS. 1 and 2 or a curved surface as shown in FIGS. 5 and 6. The raised bottom face need not be a flat surface, as long as a positive-reaction agglutinate located on the top face of the fluidal separation layer can be observed upward from the bottom of the transparent container main body. However, it is preferable that the raised bottom face has at least a flat surface region, because the flat surface region enables easy observation of the positive-reaction agglutinate in the direction from the container bottom face. Further, it is preferable that the raised bottom face has at least a curved surface region, because the curved surface region enables easier migration of the negative unagglutinated particles toward the sloping bottom face without accumulation on the raised bottom face.

If the raised bottom face 11b shown in the sectional view of FIG. 2 is a curved surface (see FIGS. 5 and 6), the boundary between the sloping bottom face and the raised bottom face is not distinct. In this case, the "raised bottom face" is determined by observing the positive-reaction agglutinate (located on the top face of the fluidal separation layer) from the bottom of the transparent container main body by eye, and determining a part of the bottom face where the fluidal separation layer is thin and the positive-reaction agglutinate can be observed by eye.

The width of the raised bottom face 11b (indicated by "w" in FIG. 2) needs to be a sufficient width to allow observation of the positive agglutination pattern from the bottom of the transparent container main body by eye. The width is preferably 1 mm or more, and more preferably, ½ or less of the width of the transparent container main body, and still more preferably ⅓ or less of the width of the transparent container main body, in order to distinguish definitely the positive and negative agglutination patterns.

The insoluble particles, which are filled inside the transparent container main body 11 and where agglutination particles are separated depending on the degree of agglutination, are not particularly limited, as long as the insoluble particles are those used in conventional microcolumn agglutination methods. Insoluble particles higher in specific gravity are easier to handle, but the insoluble particles are not particularly limited thereto. A porous material may be used as the insoluble particles, as described in EP797097. A glass bead or a crosslinked polymer is preferably used as the insoluble particles. The insoluble particle diameter is preferably 25 to 200 μm. The insoluble particle is preferably transparent in order to enable easier observation of the agglutination pattern, but may be opaque as long as the agglutination pattern can be observed.

The insoluble particles are filled in the transparent container main body 11, forming the fluidal separation layer 12. The insoluble particles are filled up to a height at least as high as the raised bottom face. The insoluble particles are filled at most to a height to give a fluidal separation layer having a thickness (indicated by "t" in FIG. 2) of preferably 2 mm, more preferably 1 mm, over the raised bottom face. When the thickness (t) of the fluidal separation layer over the raised bottom face 11b is large, the positive agglutination pattern formed on the top face of the fluidal separation layer is hard to be observed through the bottom face of the transparent container main body.

A sample inlet 13 is attached on the internal wall of the transparent container main body 11 for the purpose of addition of an antibody- or antigen-containing sample onto the raised bottom face 11b of the transparent container main body 11. The sample-introduction space of the sample inlet may function as a reaction space for a reaction between blood cells and a sample. The particle agglutination-evaluating container according to the present invention may have a sample inlet integrated with the transparent container main body, as shown in FIG. 1. The sample inlet may have a funnel shape, as shown in FIG. 1. The sample inlet may have a shape incorporable with the transparent container main body, as shown in FIG. 6. When the sample inlet is incorporated with the transparent container main body as above, it is possible to prevent scattering of the sample, by making the top space of the fluidal separation layer tightly closed.

In the present invention, the fluidal separation layer 12 may contain a reagent for an immunological test (such as antiserum), and insoluble particles may be suspended in such a reagent solution. Specifically, the fluidal separation layer 12 may contain an anti-A or anti-B serum causing an agglutination reaction with red blood cells in a sample solution. Alternatively, the fluidal separation layer 12 may contain a blood cell-reactive reagent (antiserum) such as an antiglobulin serum. The antiglobulin serum is used, for example, for detection of an antibody that does not agglutinate even by a reaction with an antigen on red blood cells (imperfect antibody). In this case, the antibody is crosslinked by addition of an antiglobulin serum as a secondary antibody after the antigen-antibody reaction, thereby causing agglutination with the red blood cells (indirect antiglobulin test (IAT)). An antiglobulin serum is contained in the insoluble particle layer, a reaction between red blood cells and the antibody (imperfect antibody) is preformed in a separate reaction chamber, and then the mixture is centrifuged. As a result of the centrifugation, only the blood cells (and the antibody bound thereto) migrate into the insoluble particle layer under the influence of their specific gravity, and react with the antiglobulin serum in the insoluble particle layer, thereby forming an agglutinate. In this way, an antiserum is added to the fluidal separation layer, and thereby it is possible to carry out IAT, without performing washing process of the red blood cells (B/F separation) needed for removing excessive antibodies not bound to the red blood cells.

Figure 3:
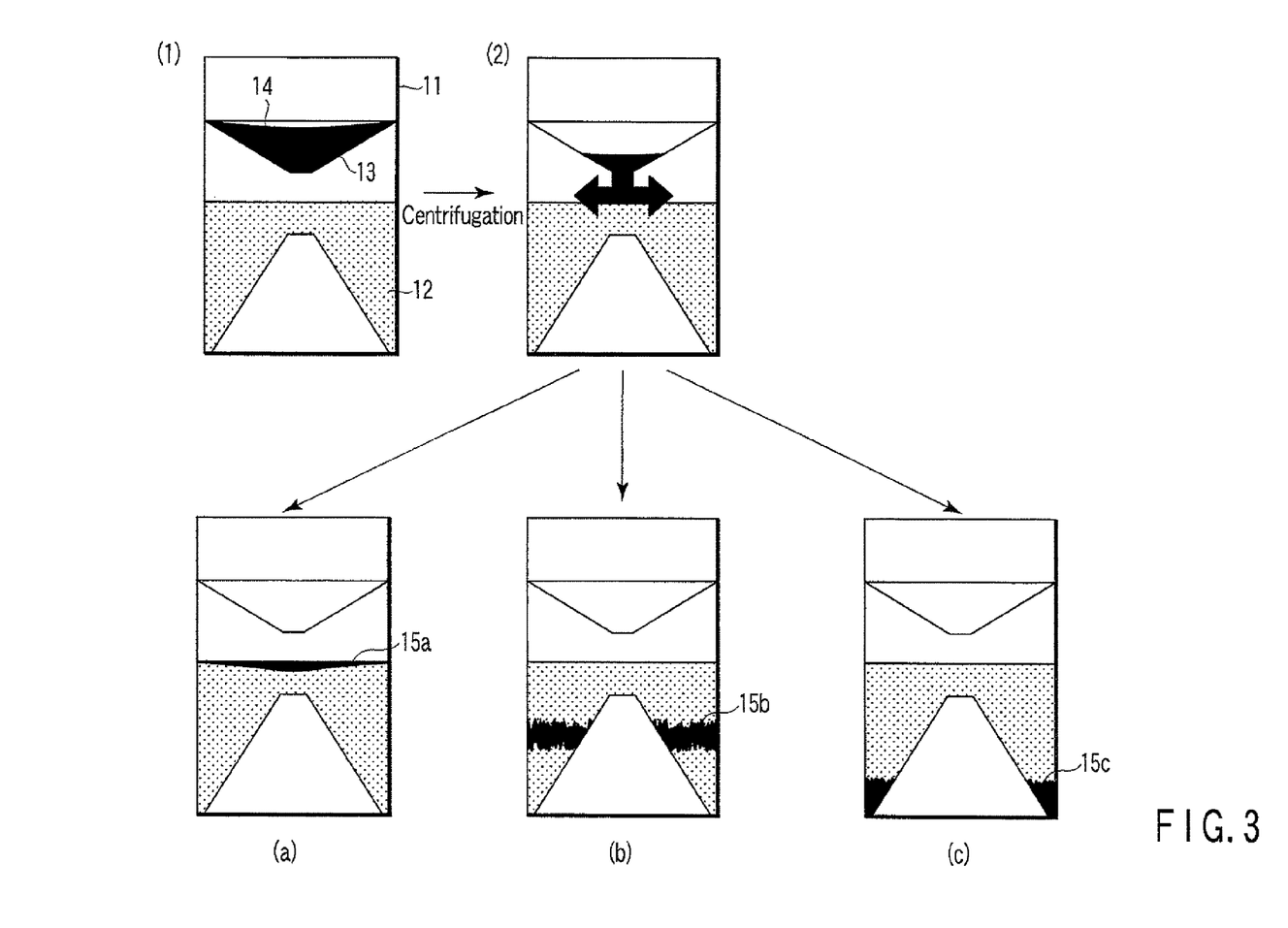
FIG. 3 shows schematic sectional views of the agglutination patterns of (a) positive, (b) weakly positive, and (c) negative reaction, in the case of a test using the particle agglutination-evaluating container according to the first embodiment of the present invention.

Hereinafter, an example of an agglutination reaction using the particle agglutination-evaluating container of the first embodiment will be described. Here, a passive agglutination method will be described, but application of the container according to the present invention is not limited thereto. First, antigen- or antibody-bound agglutination particles such as latex particles or red blood cells are reacted with a sample containing an antibody or antigen binding to the antigen or antibody bound on the agglutination particles, for a desired period in the sample-introduction space of the sample inlet 13. Alternatively, the agglutination particles are reacted with the sample beforehand for a desired period in a separate container, and then, the mixture is introduced to the sample inlet (FIG. 3(1)). In the present invention, the agglutination particles are preferably colored for visual observation of the agglutination pattern. The agglutination particles may be naturally colored, like red blood cells, or artificially colored by a known method (for example with a colorant). Alternatively, the agglutination particles may be labeled by a label (such as a fluorescent label) enabling monitoring of the position thereof in the fluidal separation layer. In FIG. 3(1), the reaction solution containing the agglutination particles and the sample is indicated by reference numeral 14.

Next, the container containing the reaction solution 14 of the agglutination particles and the sample is centrifuged. As a result of the centrifugation, the reaction solution migrates on the fluidal separation layer 12 and then precipitates toward the sloping bottom face according to the agglutination pattern (FIG. 3(2)). The centrifugation condition may vary according to the gradient angle of the sloping bottom face and the kind of the used insoluble particles, but is preferably 70 G to 300 G for 5 to 10 minutes. The centrifugation force G is preferably lower for obtaining a positive agglutination pattern, and thus, centrifugation at 70 G to 115 G is still more preferable.

Figure 4:
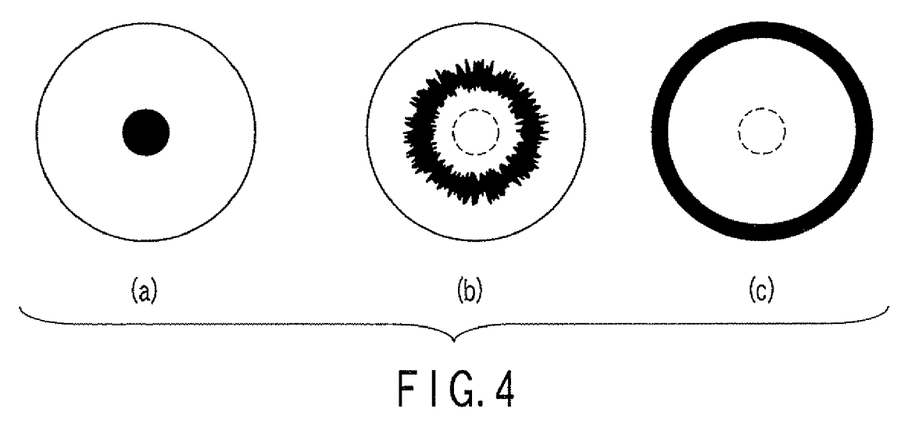
FIG. 4 shows views of the agglutination patterns of (a) positive, (b) weakly positive, and (c) negative reaction observed from below the container, in the case of a test using the particle agglutination-evaluating container according to the first embodiment of the present invention.

Examples of the agglutination patterns obtained in the agglutination reaction are schematically shown in FIGS. 3(a) to (c) and 4. FIG. 3 shows agglutination patterns in a sectional view similar to that in FIG. 2, and FIG. 4 shows agglutination patterns observed from the bottom. In the present invention, the observation of the agglutination pattern may be performed visually by naked eye when colored agglutination particles are used, but may instead be performed under microscope.

In the case of a positive reaction of strong agglutination, an agglutinate 15a is captured on the fluidal separation layer 12

(FIG. 3(a)). When this agglutination pattern is observed from the bottom face side of the container, the agglutinated particles can be observed clearly only in the region of the raised bottom face, because the thickness of the insoluble particles deposited on the raised bottom face is smaller than the thickness of the insoluble particles deposited on the sloping bottom face (FIG. 4(a)). On the other hand, in the case of a negative reaction, unagglutinated particles 15c precipitate to the bottom of the fluidal separation layer (FIG. 3(c)). When this agglutination pattern is observed from the bottom face side of the container, unagglutinated particles can be observed in the peripheral region of the transparent container main body 11 (FIG. 4(c)). On the other hand, in the case of a weakly positive reaction of relatively weak agglutination, a weakly positive agglutinate 15b is captured in the intermediate region of the fluidal separation layer 12 (FIG. 3(b)). When this agglutination pattern is observed from the container bottom face side, the intermediate agglutination pattern between positive and negative agglutination patterns can be identified (FIG. 4(b)).

As described above, it is possible to evaluate the agglutination pattern accurately and easily from the bottom face side of the container, by making the bottom face of the container into an inverted-V shape of a truncated circular cone and making the most highly raised bottom face into a horizontal face.

The particle agglutination-evaluating container according to the present invention may be expressed as "a container comprising a container main body with a transparent raised bottom face having a mountain-like shape and a fluidal separation layer containing insoluble particles which are filled in the transparent container main body and where the agglutination particles are separated according to the degree of agglutination". The mountain-like shape may be a shape of a truncated cone (see FIG. 2), or a shape of a truncated cone having a rounded raised bottom face (see FIGS. 5 and 6).

Figure 11:
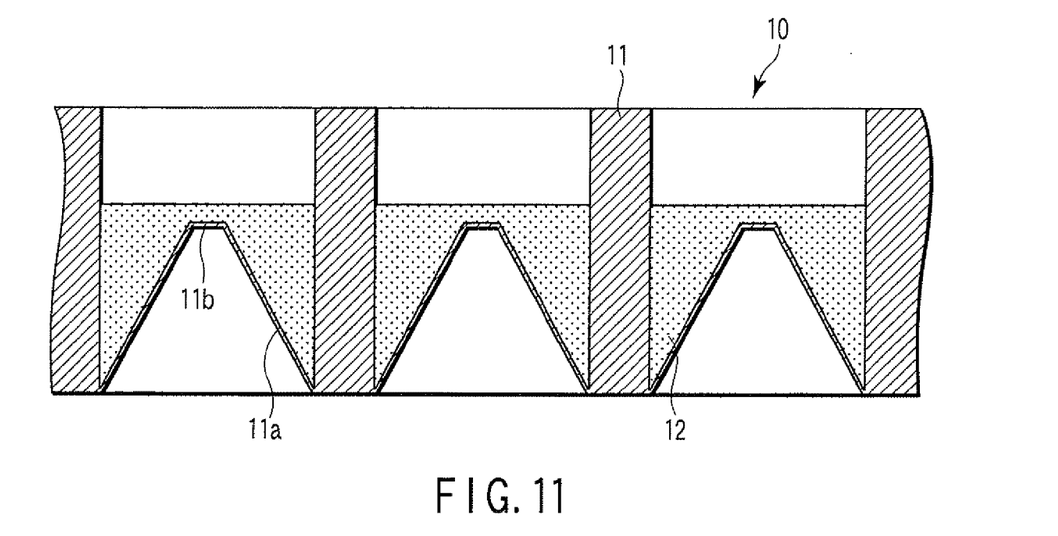
FIG. 11 is a sectional view illustrating an example of a particle agglutination-evaluating container having multiple particle agglutination-evaluating containers of the present invention aligned in parallel with each other.

Multiple containers of the present invention are aligned longitudinally and latitudinally, for example, aligned according to an alignment of wells of 96-well plate, to make a container assembly, and thereby the agglutination patterns of multiple samples can be observed from the bottom of the container assembly at the same time. FIG. 11 shows the sectional view of an example of the agglutination-evaluating container having multiple containers of the present invention aligned in parallel. The agglutination-evaluating container shown in FIG. 11 has multiple wells; and each container corresponding to each well has a transparent container main body 11 including a sloping bottom face 11a and a raised bottom face 11b extended in a horizontal direction at the top of the sloping bottom face to form an obtuse angle with the sloping bottom face, and a fluidal separation layer 12 containing insoluble particles which are filled in each well and where the agglutination particles are separated according to the degree of agglutination.

As described above, it is possible to observe agglutination patterns of multiple samples from the bottom of the container assembly at the same time, by placing multiple containers of the present invention aligned longitudinally and latitudinally, for example, aligned according to an alignment of wells of 96-well plate.

MODIFIED EXAMPLES

Hereinafter, modified examples of the particle agglutination-evaluating container according to the first embodiment of the present invention will be described. In the modified examples, only the points different from the first embodiment of the present invention will be described.

A sectional view of a particle agglutination-evaluating container of modified example 1 is shown in FIG. 5 in which the flat raised bottom face in the first embodiment is replaced with a rounded raised bottom face. The rounded raised bottom face enables migration of negative unagglutinated particles toward the sloping bottom face without accumulation on the raised bottom face.

A sectional view of a particle agglutination-evaluating container of modified example 2 is shown in FIG. 6, in which the inverted-V shape of the truncated circular cone in the first embodiment is replaced with an inverted-U shape and the gradient angle of the sloping bottom face is changed to increase in the region closer to the bottom. Further, in the modified example 2, the sample inlet 13 is separated from the transparent container main body 11 and used as it is connected to the transparent container main body with screwing or pushing, whereas the sample inlet is integrated with the transparent container main body in the first embodiment. According to the modified example 2, it is possible to form a negative agglutination pattern more definitely, by increasing the gradient angle of the sloping bottom face in the region closer to the bottom end of the sloping bottom face. As shown in FIG. 6, if the top space over the fluidal separation layer is sealed tightly when the sample inlet is connected to the transparent container main body, it is possible to prevent scattering of the sample.

Figure 7:
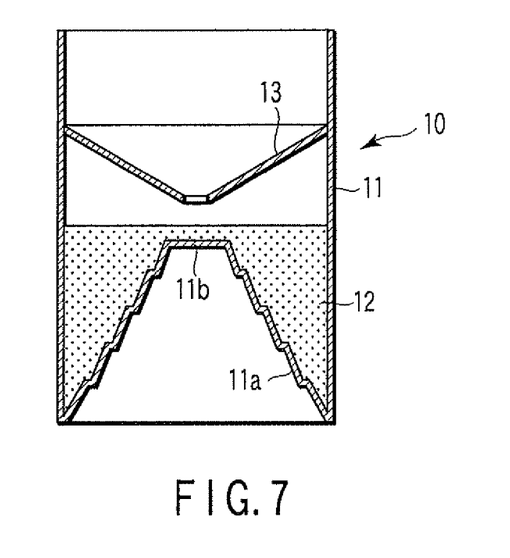
FIG. 7 is a sectional view of a modified example 3 of a particle agglutination-evaluating container according to the first embodiment of the present invention.

A sectional view of a particle agglutination-evaluating container of modified example 3 is shown in FIG. 7, in which the sloping bottom face having a smooth surface in the first embodiment is replaced with a sloping bottom face having a roughened surface. As shown in FIG. 7, the roughened surface in the modified example 3 is formed by making multiple steps different in level on the sloping bottom face. The multiple steps can increase the efficiency of capturing the weakly positive agglutinate.

Figure 8:
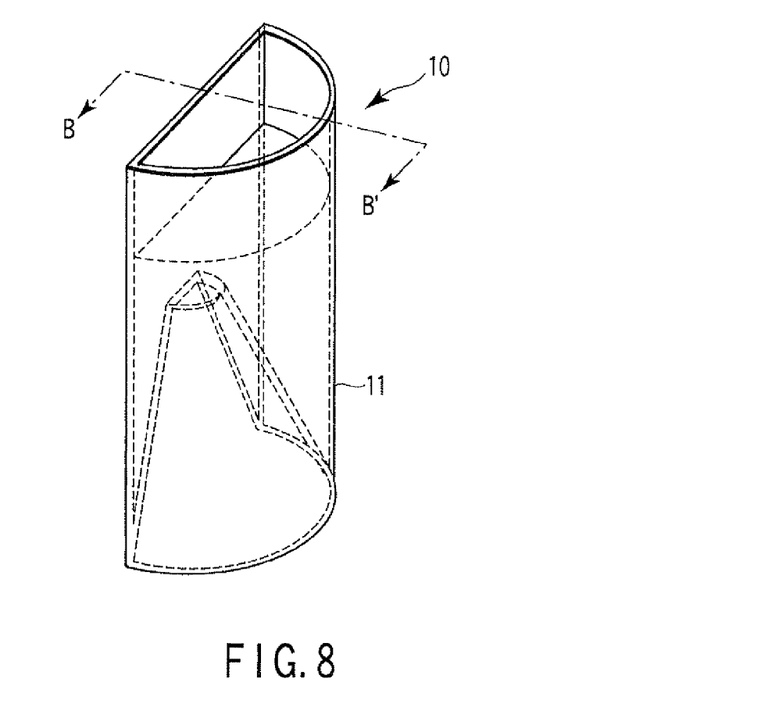
FIG. 8 is a perspective view of a modified example 4 of a particle agglutination-evaluating container according to the first embodiment of the present invention.
Figure 9:
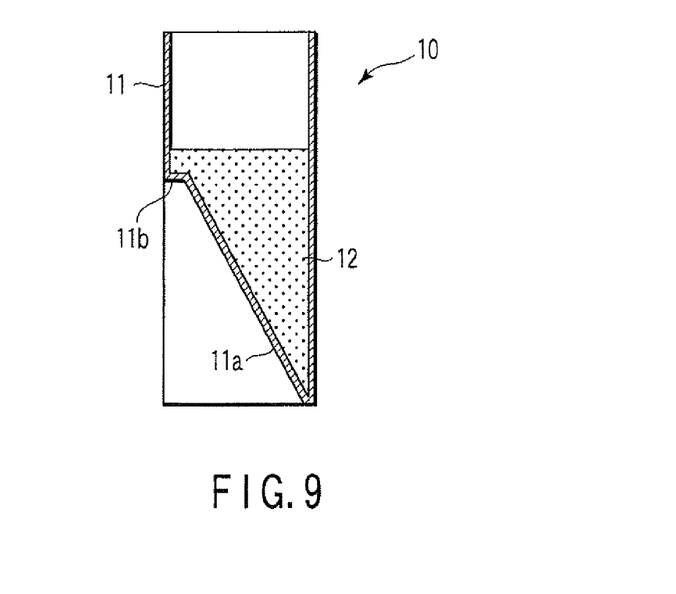
FIG. 9 is a sectional view of the container, when cut along the line B-B' shown in FIG. 8.
Figure 10:
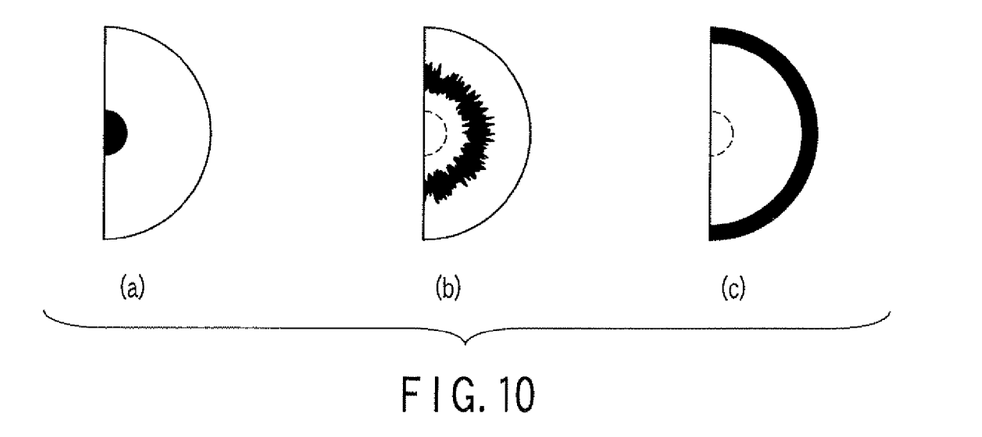
FIG. 10 shows views of the agglutination patterns of (a) positive, (b) weakly positive, and (c) negative reaction observed from below the container, in the case of a test using the particle agglutination-evaluating container according to the modified example 4 of the present invention.

A perspective view of a particle agglutination-evaluating container of modified example 4 is shown in FIG. 8, in which the cylindrical container in the first embodiment is replaced with a semi-cylindrical container. The sectional view thereof along the line B-B' shown in FIG. 8 is shown in FIG. 9. The particle agglutination-evaluating container of the modified example 4 is a container corresponding to a half of that in the first embodiment cut in the vertical direction. FIG. 10 shows the agglutination patterns of (a) positive reaction, (b) weakly positive reaction, and (c) negative reaction, observed from the bottom face side of the container, in the case of a test using the particle agglutination-evaluating container of the modified example 4. As shown in the modified example 4, it is sufficient to distinguish the respective agglutination patterns, if the transparent container main body has a bottom face including a sloping bottom face and a raised bottom face extended in a horizontal direction at the top of the sloping bottom face to form an obtuse angle with the sloping bottom face.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A particle agglutination-evaluating container for use in immunological analysis, based on an agglutinate formed in an agglutination reaction between an antibody- or antigen-containing sample and agglutination particles, comprising:
- a transparent container main body having a raised bottom including a sloping bottom face and a raised bottom face extended in a horizontal direction at the top of the sloping bottom face to form an obtuse angle with the sloping bottom face; and
- a funnel-shaped sample inlet attached on an internal wall of transparent container main body; and
- a fluidal separation layer containing insoluble particles which are filled in the transparent container main body and where the agglutination particles are separated according to the degree of agglutination,
- wherein the agglutination particles form an agglutinate and are located on a top face of the fluidal separation layer when the agglutination reaction is positive, the agglutination particles do not form an agglutinate and migrate to the bottom of the sloping bottom face when the agglutination reaction is negative, and the agglutination particles form an agglutinate and are located in an intermediate region of the fluidal separation layer when the agglutination reaction is weakly positive between positive and negative, and thus agglutination is evaluated by observation from the bottom face side of the transparent container main body, where the agglutination reaction is judged positive when the agglutination particles are observed through the raised bottom face, negative when the agglutination particles are observed at the bottom end of the sloping bottom face, and weakly positive when the agglutination particles are observed in the middle of the sloping bottom face.

2. A particle agglutination-evaluating container for use in immunological analysis, based on an agglutinate formed in an agglutination reaction between an antibody- or antigen-containing sample and agglutination particles, comprising:
- a transparent container main body having a raised bottom raised in a shape of a truncated cone or pyramid, where the raised bottom face includes a sloping bottom face and the vertex region of the bottom face forms a raised bottom face extended in a horizontal direction in the vertex region of the raised bottom; and
- a funnel-shaped sample inlet attached on an internal wall of transparent container main body; and
- a fluidal separation layer containing insoluble particles which are filled in the transparent container main body and where the agglutination particles are separated according to the degree of agglutination,
- wherein the agglutination particles form an agglutinate and are located on a top face of the fluidal separation layer when the agglutination reaction is positive, the agglutination particles do not form an agglutinate and migrate to the bottom of the sloping bottom face when the agglutination reaction is negative, and the agglutination particles form an agglutinate and are located in an intermediate region of the fluidal separation layer when the agglutination reaction is weakly positive between positive and negative, and thus agglutination is evaluated by observation from the bottom face side of the transparent container main body, where the agglutination reaction is judged positive when the agglutination particles are observed through the raised bottom face, negative when the agglutination particles are observed at the bottom end of the sloping bottom face, and weakly positive when the agglutination particles are observed in the middle of the sloping bottom face.

3. The particle agglutination-evaluating container according to claim 2, wherein the bottom face of the transparent container main body includes a sloping bottom face raised in a shape of a truncated circular cone, where the vertex region of the bottom face forms a raised bottom face extended in a horizontal direction.

4. The particle agglutination-evaluating container according to claim 1, wherein the raised bottom face is a flat surface.

5. The particle agglutination-evaluating container according to claim 1, wherein a thickness of the fluidal separation layer deposited on the raised bottom face of the transparent container main body is 2 mm or less.

6. The particle agglutination-evaluating container according to claim 1, wherein the gradient angle of the sloping bottom face of the transparent container main body is 45° to 75° with respect to the horizontal plane.

7. The particle agglutination-evaluating container according to claim 1, wherein the gradient angle of the sloping bottom face of the transparent container main body increases in a region closer to the bottom of the sloping bottom face.

8. The particle agglutination-evaluating container according to claim 1, wherein a width of the raised bottom face is ½ or less of a width of the transparent container main body, when the transparent container main body is observed from a side wall direction.

9. The particle agglutination-evaluating container according to claim 1, wherein the sample inlet injects an antibody- or antigen-containing sample collectively onto the fluidal separation layer deposited on the raised bottom face.

10. The particle agglutination-evaluating container according to claim 1, wherein the sloping bottom face of the transparent container main body is surface-roughened.

11. The particle agglutination-evaluating container according to claim 1, wherein the insoluble particles are glass bead or crosslinked polymer particles and the particle diameter is 25 to 200 μm.

12. The particle agglutination-evaluating container according to claim 1, wherein the fluidal separation layer contains an antiserum.

13. A particle agglutination-evaluating container for use in immunological analysis of a plurality of samples, based on an agglutinate formed in each agglutination reaction between a plurality of antibody- or antigen-containing samples and a plurality of kinds of agglutination particles corresponding to the respective samples, wherein the container has a plurality of wells, and each well comprises transparent well main body having a raised bottom including a sloping bottom face and a raised bottom face extended in a horizontal direction at the top of the sloping bottom face to form an obtuse angle with the sloping bottom face, a funnel-shaped sample inlet attached on an internal wall of transparent container main body; and a fluidal separation layer containing insoluble particles which are filled in the each well and where the agglutination particles are separated according to the degree of agglutination.

14. A particle agglutination-evaluating container for use in immunological analysis, based on an agglutinate formed in an agglutination reaction between an antibody- or antigen-containing sample and agglutination particles, comprising:
- a container main body having a transparent raised bottom which is raised in a mountain-like shape;
- a funnel-shaped sample inlet attached on an internal wall of transparent container main body; and a fluidal separation layer containing insoluble particles which are filled in the transparent container main body and where the agglutination particles are separated according to the degree of agglutination.

15. A particle agglutination-evaluating container for use in immunological analysis of a plurality of samples, based on an agglutinate formed in each agglutination reaction between a plurality of antibody- or antigen-containing samples and a plurality of kinds of agglutination particles corresponding to the respective samples, wherein the container has a plurality of wells, and each well comprises a well main body having a transparent raised bottom which is raised in a mountain-like shape, a funnel-shaped sample inlet attached on an internal wall of transparent container main body; and a fluidal separation layer containing insoluble particles which are filled in the each well and where the agglutination particles are separated according to the degree of agglutination.

* * * * *